United States Patent [19]
Ohta

[11] Patent Number: 6,086,832
[45] Date of Patent: Jul. 11, 2000

[54] APPARATUS FOR EVALUATING A SOLID CATALYST AND EVALUATION METHOD USING THE APPARATUS

[75] Inventor: Nobuyuki Ohta, Sodegaura, Japan

[73] Assignee: Idemitsu Kosan Co., Ltd., Tokyo, Japan

[21] Appl. No.: 08/986,756

[22] Filed: Dec. 8, 1997

[30] Foreign Application Priority Data

Dec. 6, 1996 [JP] Japan ..................................... 8-327339

[51] Int. Cl.⁷ ...................................................... B01J 8/02
[52] U.S. Cl. ........................ 422/211; 422/106; 422/222; 422/224; 422/225; 422/242; 436/37
[58] Field of Search ................................... 422/106, 226, 422/211, 108, 110, 187, 188, 189, 190, 193, 205, 222, 224, 225, 228, 231, 242, 68.1; 436/37

[56] References Cited

U.S. PATENT DOCUMENTS 4,937,051 6/1990 Graven et al. ........................... 422/194
5,133,941 7/1992 Hays et al. ............................... 422/140

*Primary Examiner*—Marian C. Knode
*Assistant Examiner*—Frederick Varcoe
*Attorney, Agent, or Firm*—Oblon, Spivak, McClelland, Maier & Neustadt, P.C.

[57] ABSTRACT

An apparatus for evaluating a solid catalyst which can enlarge a range of an applied fluid used for an evaluation of a performance of the solid catalyst and can accurately evaluate the performance of the solid catalyst on a laboratory scale and a method of evaluating a solid catalyst using the apparatus are provided. There are disclosed an apparatus of evaluating a solid catalyst, wherein a raw material feeding portion has a function capable of continuously feeding a liquid raw material or a mixed raw material consisting of a gas and a liquid, wherein a reactor in a reacting portion has an inlet for a fluid raw material and reaction product outlets for discharging a reaction product while separating it into a liquid product and a gaseous product, and wherein a recovering portion has reaction product inlets connected to each of the reaction product outlets of the reactor and has a liquid level control portion for keeping a liquid level within the reactor constant, and a method of evaluating a solid catalyst using the apparatus.

11 Claims, 4 Drawing Sheets

APPARATUS FOR EVALUATING A SOLID CATALYST AND EVALUATION METHOD USING THE APPARATUS

FIELD OF THE PRESENT INVENTION

The present invention relates to an apparatus for evaluating a solid catalyst and a method of evaluating a solid catalyst. More particularly, the present invention relates to an apparatus for evaluating a solid catalyst and a method of evaluating a solid catalyst using the apparatus, which are suitably used in a type of industry where a product is manufactured by a reaction apparatus using the solid catalyst, for example, an oil refining industry, a petrochemical industry, the whole field of organic and inorganic chemical industry, and a testing, research, development and quality control field with respect to a catalyst in a design, construction industry and a manufacturing industry for a solid catalyst.

BACKGROUND OF THE PRESENT INVENTION

Conventionally, as an apparatus for evaluating an activity and life of a solid catalyst, a selectivity of a product and a quality of a product on a laboratory scale, an apparatus using an isothermal tubular reactor is frequently used.

As disadvantages of this tubular reactor, the following points have been indicated.

(1) Since a flow rate is lower than that of a large scale tubular reactor (hereinafter, referred to as an actual apparatus) used for an commercial purpose, the apparatus is effected by a mass transport limitation, so that there is a fear that the obtained evaluation results are different from that of the actual apparatus.

(2) When a diameter of the tube is too small, the apparatus is significantly effected by a maldistribution due to the wall, and when a length of a packing layer is too short, the apparatus is significantly effected by a back mixing.

(3) In a system of great endothermic reaction or great exothermic reaction, not only it is hard to maintain an isothermal condition, but also a difference is generated between a surface temperature of the catalyst (an actual reaction temperature) and a temperature of a fluid, so that it is hard to recognize the actual reaction temperature.

(4) Since the structure is made such that the fluid is successively reacted from an inlet to an outlet of the catalyst layer, a concentration of a material to be reacted, a reaction rate and a concentration of a poisoning material collected on the catalyst are largely different when seen in a finely divided section. Accordingly, it is hard to accurately obtain a reaction rate and a deterioration characteristic of the catalyst.

Therefore, hitherto, it has been a common sense that as well as the scale of the experimental apparatus has been gradually enlarged, the research and development has been proceeded while recognizing the influences of the above items (1) to (4).

Further, there has been suggested various kinds of evaluation apparatuses using a reactor each of which is designed for the purpose of solving the disadvantages of the above items (1) to (4) on a laboratory scale. The apparatus will be described below while indicating the source thereof.

(1) Berty Reactor
 1) Berty, J. M. et al.; 64th National Meeting A. I. Ch. E Preprint 42E (1969)

There are shown evaluation results (hydrogenation of ethylene) in the case that a fluid in a 5 inch type reactor (named at the later time) is a gas phase and a chart for calculating a flow rate of a gas passing through a catalyst layer.

A summary of applied examples published later is shown in Table 1 together with cited references.

TABLE 1

| Reaction used | Purpose of research | Condition of reaction | References |
|---|---|---|---|
| Hydrogenation of ethylene | Recognition of performance of reactors | 100° C. 10–20 atm | 2), 4) |
| Synthesis of methanol | Consideration of runaway condition | 232° C. 52 atm | 5) |
| Synthesis of methanol | Consideration of catalyst species and catalysis | 255° C. 16 atm | 8) |
| Dehydrogenation of cyclohexanol | Consideration of reaction kinematics | 270–380° C. 1–2 atm | 6) |
| Aromatization of n-heptane | Recognition of deteriorating behavior | 370–590° C. | 7) |
| CO oxidation | Consideration of kinematic model Verification of optimum control model | 160–200° C. | 9) |
| Methanation of CO | Consideration of deteriorating rate equation | 237–337° C. 69 atm | 10) |
| Sublimation of naphthalene | Recognition of performance of reactor | 23° C. 0.87 atm | 11) |
| Oxidation of $SO_2$ | Consideration of kinematic equation | 363–363° C. 2.5–10 atm | 12) |

References
2) Berty J. M. et. al., AIChE 64th National Meeting 42E (1969)
4) Berty J. M. , Chem. Eng. Prog., 70(5), 78 (1974)
5) Berty J. M. et. al., AIChE J., 28(6), 914 (1982)
6) Gut G. et. al., Chem. Eng. Sci., 37(2), 319 (1982)
7) Mahoney J. A., J Catal., 32, 247 (1974)
8) Kelly K. P. et. al., J Catal., 101, 396 (1986)
9) Broucek R. et. al., Chem. Eng. Sci., 41(11), 2901 (1986)
10) Bowman R. M. et. al., Appli. Catalysis, 7, 179 (1983)
11) Caldwell L., Appli. Catalysis. 8, 199 (1983)
12) Doering F. J., Chem. Eng. Sci., 43(2) 221 (1988)

2) "Continuous Operation Of The Berty Reactor For The Solvent Methanol process" Berty J. M., Tnd. Eng. Chem. Res. 30,1413–1418 (1991)

A method of successively evaluating a catalyst by introducing a synthesis gas under a state of fully filling the Berty reactor with a solvent is disclosed.

(2) Spinning Basket Reactor
 1) Myers, E. C. et al.; A. C. S. Sympo. No. 65 37 (1978)

A desulfuration reaction rate of dibenzothiophene contained in white oil is measured by using a Multi Phase spinning Basket Reactor (a name in the reference). Further, a method of performing an experiment is explained relatively in detail.

2) Ammus, J. M. et al; I. E. C. Res. 26, 494–501 (1987)

A desulfuration reaction rate of atmospheric residual oil is measured by using a spinning Basket Reactor (a name in the reference). Further, a method of performing an experiment is explained relatively in detail.

Since a liquid surface within a spinning basket reactor is not largely changed, it is considered that a successive evaluation experiment on a catalyst of three phases of gas, liquid and solid by means of the reactor can be easily performed.

(3) Other Internal Recycle Reactors of Fixed Catalyst Type

1) Jankowski, H. et al.; Chem. Techn. (Berlin) 30, 9, 441–446 (1978)

Various kinds of internal recycle reactors (Gradientless Laboreactor) published at this point of time are introduced.

2) Brown, C. E. et al.; A. I. Ch. E. J. 16 (5). 817–822 (1970)

A reaction rate of gas phase methanol synthesis is obtained by a self-made internal recycle reactor.

(4) Autoclave

As a technique similar to the internal recycle reactor, a method of evaluating a solid catalyst in a gas phase or a liquid phase by using an autoclave has been known by those skilled in the art for a long time.

However, in the Berty reactor mentioned in the above item (1), the reactor mentioned in the item 1) treats only a gas phase reaction system. Further, the method described in the item 2) has the following disadvantages.

(a) A solvent in a liquid phase is not successively discharged.

(b) Since the reactor is fully filled with the liquid, an interface area between the gas and the liquid is insufficient so that a mass transfer from the gas phase is liable to become a rate-determining.

(c) Since the reaction gas is introduced from a lower portion of a magnetic agitator, when the gas introduction rate is increased, there is a case that the impeller moves upward so as to come into contact with a catalyst basket, thereby leading to a breakage. The inventors have actually experienced the breakage of the impeller.

(d) Since a gaseous raw material and a solvent are respectively introduced into a reactor from separate inlets, in the event that the solvent is a heavy oil (for example, an atmospheric residual oil), there is a case that a coking is effected during a process of passing through the inlet portion of the reactor, thereby leading to a plugging. The inventors have actually experienced the plugging.

Further, in the Spinning basket reactor mentioned in the above item (2), the reactors described in the items 1) and 2) have the following disadvantages.

(a) Since the fluid is rotated together with the catalyst basket, an actual flow rate of the fluid with respect to the catalyst can not be evaluated.

(b) When the flow rate can not be evaluated, a mass transfer rate between the gas and the liquid or between the liquid and the solid becomes unclear, so that a intrinsic reaction rate can not be obtained.

(c) Since it is significantly difficult to fix a center of the basket when packing the basket with the catalyst, if the basket filled with the catalyst is rotated at a high speed, a bearing supporting a drive shaft is worn during a short period of time, so that it is not suitable for evaluating a catalyst for several months.

(d) In FIG. 3 of the reference "An Improved Gas Recirculation Reactor For Catalystic Studies", Caldwell, L.; Apply. Catal. 8. 199–213 (1983), it is pointed out that the spinning basket type (this is called as Carberry type in the reference) has less performance than the Berty type.

Further, in the other internal recycle reactors of fixed catalyst type mentioned in the above item (3), both of the reactors described in the items 1) and 2) do not disclose the applied reaction system.

Still further, the autoclave mentioned in the above item (4) mostly performs a screening test of the catalyst in a batch operation, so that it is impossible to obtain data having such a high accuracy as in a continuous operation. Further, although there is an example of evaluating by a continuous operation in such a manner as not to change a liquid surface within the reactor in the same manner as the spinning basket, in the case that the catalyst is not fixed, since a diameter of a particle of the catalyst is changed during the reaction, a correctly evaluated result can not be obtained, and also in the case that the catalyst is fixed by using a cage or a net, since a chart for evaluating a rotating speed and a flow rate when the fluid passes through the catalyst layer as in the Berty reactor is not disclosed, the flow rate can not be evaluated as well.

As mentioned above, in all of the conventional evaluating apparatuses, in the case that a fluid to be evaluated is a liquid phase or a gas-liquid phase, since it is difficult to continuously discharge the evaluated fluid, the apparatus is exclusively used for a gas phase reaction system.

However, it has been strongly desired for a long time to enlarge a range of the fluid to be applied to a liquid phase or a gas-liquid phase in various kinds of technical fields in which it is necessary to use a solid catalyst and to perform various kinds of reactions in a liquid phase or a gas-liquid phase for the purpose of tests and researches.

Incidentally, as a method of evaluating a catalyst under a liquid phase and a gas-liquid phase in the Berty reactor, although the following two references disclose an information that an evaluation of a catalyst under a liquid phase and a gas-liquid phase can be performed, in any of these references, a concrete method thereof is not disclosed.

1) Ohta; Idemitsu Technical Report, 34 (4), 397–402 (1991)

2) 3" Catalytic reactors catalogue No.3821 autoclave engineer company

SUMMARY OF THE PRESENT INVENTION

The present invention is achieved by taking the above problems into consideration, and an object of the present invention is to provide an apparatus for evaluating a solid catalyst which enlarges a range of an applied fluid used for an evaluation of a performance of the solid catalyst and can accurately estimate the performance of the solid catalyst on a laboratory scale and a method of evaluating a solid catalyst using the apparatus.

In order to achieve the above object, according to the present invention, there is provided an apparatus for evaluating a solid catalyst comprising a raw material feeding portion for feeding a fluid raw material, a reacting portion having a reactor which brings the fed fluid raw material into contact with a solid catalyst disposed within the reactor so as to react therewith, and a recovering portion for recovering a reaction product fed from the reacting portion, wherein the raw material feeding portion has a function capable of continuously feeding a liquid raw material or a mixed raw material consisting of a gas and a liquid, wherein the reactor in the reacting portion has an inlet for the fluid raw material and reaction product outlets for discharging the reaction product while separating it respectively into a liquid product and a gaseous product, and wherein the recovering portion has reaction product inlets connected to each of the reaction product outlets of the reactor and has a liquid level control portion for keeping a liquid level within the reactor constant.

Further, as a preferred mode of the present invention, there is provided an apparatus for evaluating a solid catalyst, wherein the recovering portion has the reaction product inlets and the liquid level control portion and further has a gas-liquid separating portion for separating the reaction product fed from the liquid level control portion into a gas and a liquid.

Still further, as a preferred mode of the present invention, there is provided an apparatus for evaluating a solid catalyst, wherein the reactor in the reacting portion is an internal recycle reactor of a fixed catalyst type.

Furthermore, as a preferred mode of the present invention, there is provided an apparatus for evaluating a solid catalyst, wherein the liquid level control portion is a control tank of an overflow type.

Moreover, according to the present invention, there is provided a method of evaluating a solid catalyst by using the apparatus for evaluating a solid catalyst, comprising a step of bringing the fluid raw material in the reacting portion into contact with the solid catalyst under a state of liquid phase or gas-liquid phase, and a step of continuously discharging the reaction product.

Further, as a preferred mode of the present invention, there is provided a method of evaluating a solid catalyst, wherein the fluid raw material is a group of oils or a mixed fluid of a group of oils and hydrogen.

DESCRIPTION OF THE PREFERRED EMBODIMENT

An embodiment of the present invention will be concretely described below with reference to the drawings.

Figure 1:
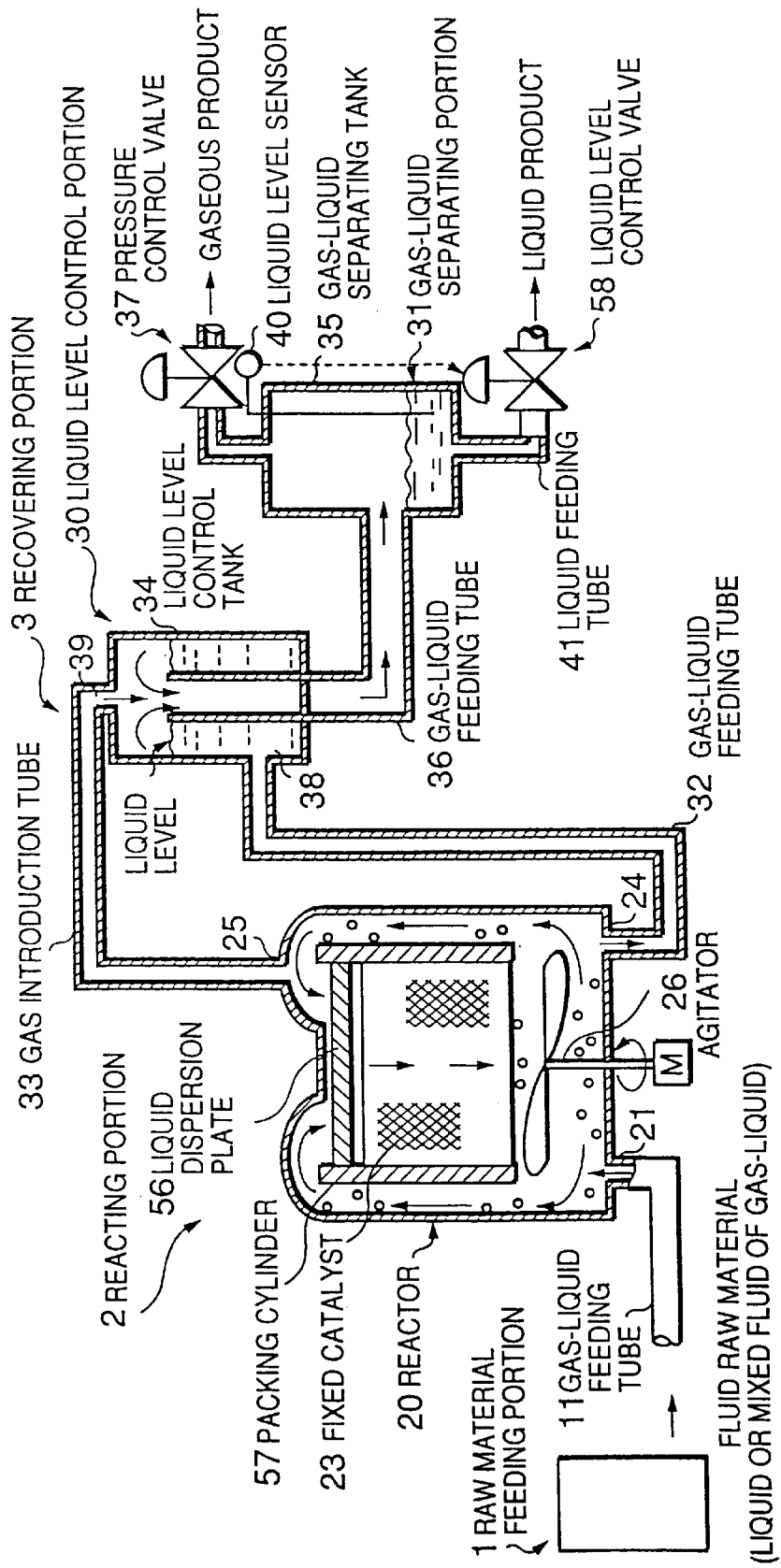
FIG. 1 is an explanatory view which shows schematically an embodiment of an apparatus for evaluating a solid catalyst in accordance with the present invention.

FIG. 1 is an explanatory view which shows schematically an embodiment of an apparatus for evaluating a solid catalyst in accordance with the present invention.

Figure 2:
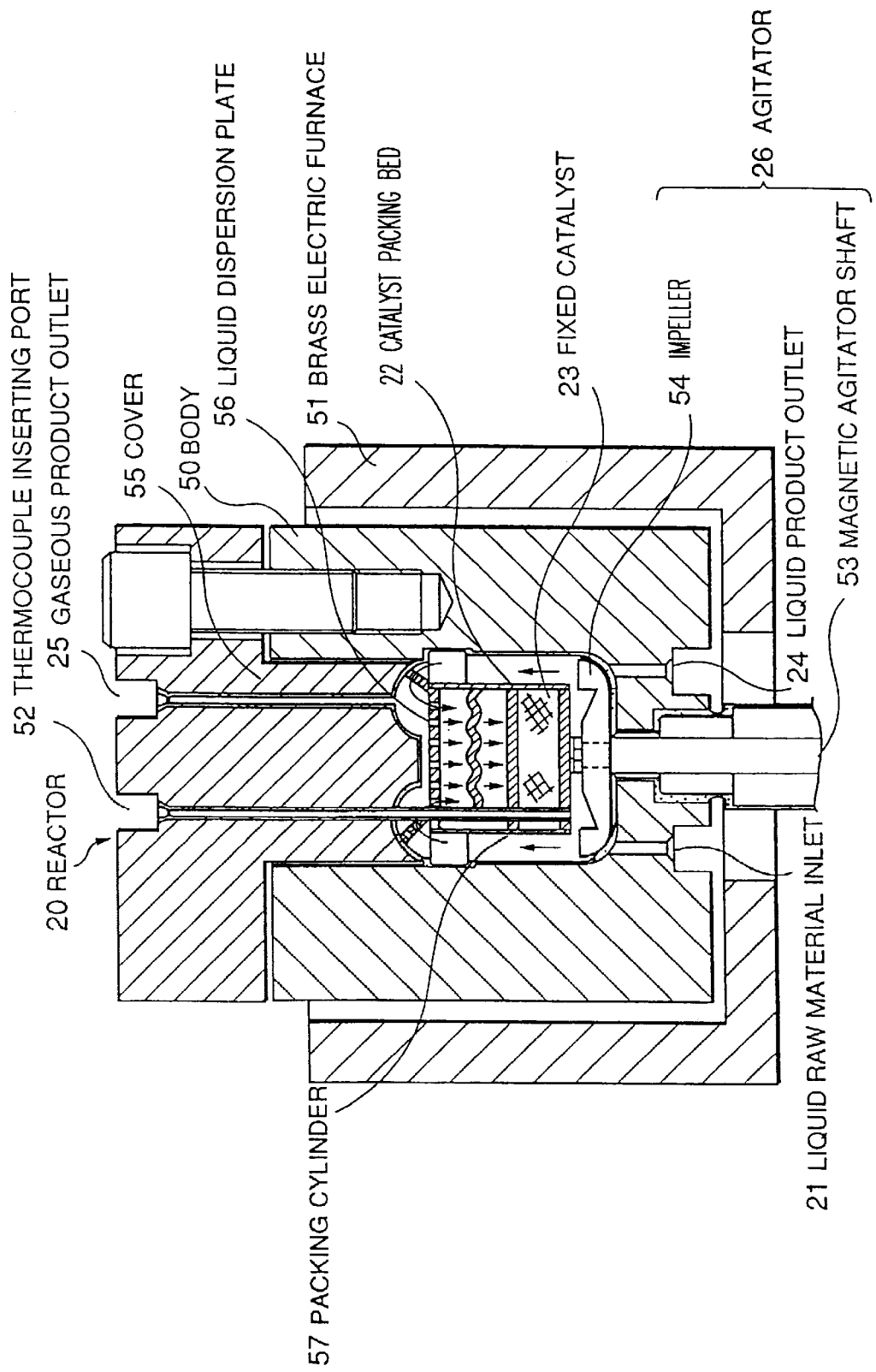
FIG. 2 is an explanatory cross-sectional view which shows schematically an embodiment of an internal recycle reactor used in the present invention.

FIG. 2 is an explanatory cross-sectional view which shows an embodiment of an internal recycle reactor used in the present invention.

I. Apparatus for Evaluating a Solid Catalyst

As shown in FIG. 1, an apparatus for evaluating a solid catalyst in accordance with the present invention is mainly constituted by a raw material feeding portion 1, a reacting portion 2 and a recovering portion 3.

1. Raw Material Feed Portion

As the raw material feeding portion 1 for feeding a fluid raw material, as far as it has a function of continuously feeding a liquid raw material or a mixed raw material of a gas and a liquid, there is no special limitation. For example, there is exemplified a raw material feeding portion which has a liquid raw material feeding portion and a gas raw material feeding portion and which is capable of switching the fluid to be fed. By structuring in this manner, a fluid raw material to be fed to the next reacting portion 2 can be made into three kinds of a gas, a liquid and a gas-liquid mixture.

Here, as a liquid raw material fed from the liquid raw material feeding portion, for example, a group of oils or various kinds of solvents whose pressure is increased by a pump, etc. and whose flow rate is controlled by a flow meter, etc. can be exemplified. Even in the case of heavy oil such as atmospheric residual oil, etc., it can be used if a line is heated to a temperature at which it can keep fluidity.

Further, as a gas raw material fed from the gas raw material feeding portion, for example, a reaction gas such as a hydrogen or inert gas and the like whose pressure is increased to a reaction pressure by a compressor, a bomb, etc. and whose flow rate is controlled by a flow meter, etc. can be exemplified.

2. Reacting portion

The reacting portion 2 in the present invention has a reactor 20 in which a fluid raw material fed from the raw material feeding portion 1 through a gas-liquid feeding tube 11 is contacted and reacted with a fixed catalyst 23 disposed in an inner portion thereof.

(1) Reactor

As the reactor 20 used in the present invention, for example, an internal recycle reactor shown in FIGS. 1 and 2 can be exemplified. As this reactor, a tank type-agitating reactor of the system of fixing the catalyst, which has a jacket or an electric furnace and can control a reaction temperature, is preferable. Among others, a Berty reactor is preferable. Further, it may be a reactor of the system of rotating the catalyst or an autoclave. In the embodiment shown in FIGS. 1 and 2, the fluid raw material flowing from a fluid raw material inlet 21 is made into a gas-liquid mixed phase by an agitator 26 and a constant flow (in this case, a downstream flow) of the gas-liquid is formed in layers of the fixed catalyst 23, and as shown in FIG. 2 it is contacted and reacted with the catalyst fixed to a catalyst packing bed 22. Among reaction products, a liquid product is discharged from an outlet 24 disposed, for example, in the lower portion and a gaseous product from an outlet 25, for example, disposed in an upper portion.

In the embodiment shown in FIG. 2, a body 50 of the reactor 20 is surrounded by a brass electric furnace 51 and a reaction temperature can be controlled. Further, a thermocouple inserting port 52 for inserting a thermocouple used for controlling a temperature of the fixed catalyst 23 is provided in the upper portion. Still further, the body 50 of the reactor is covered by a cover 55.

Here, as the fixed catalyst 23, for example, a fixed catalyst of a heterogeneous system can be exemplified. Concretely speaking, it is preferable to fill an alumina-supported catalyst, a zeolite catalyst, an activated carbon supported carrier catalyst and the like into a packing cylinder 57 fixed within the reactor 20. Further, it is preferable to provide a porous liquid dispersion plate 56 in an upper portion of the packing cylinder 57.

By providing the liquid dispersion plate 56, a maldistribution of the fluid raw material can be prevented, so that the raw material can be uniformly brought into contact with the fixed catalyst 23.

As the agitator 26, as far as it can agitate the fluid raw material within the reactor 20, there is no special limitation, however a magnetic agitator which can keep a pressure is preferable. In the embodiment shown in FIG. 2, it is constituted by a magnetic agitator shaft 53, an impeller 54 and a driving portion (not shown). The mounting direction may be either a vertical lower direction or a vertical upper direction.

A flow rate of the fluid raw material in the layer of the fixed catalyst 23 is controlled by a shape of the impeller 54 of the agitator 26, an adjustment of the rotating speed and the like.

Further, a liquid level of the fluid raw material within the packing cylinder 57 is preferably controlled so as to be constant by discharging the liquid raw material in correspondence to the feed thereof.

Incidentally, in the case that the fluid raw material is only the liquid raw material, the constitution shown in FIG. 2 may be used as it is, or the gaseous product outlet 25 may not be used. Further, the constitution having no gaseous product outlet may be used. In this case, the position in which the liquid product outlet 24 is disposed can be provided anywhere irrespective of whether it exists in the upper portion or lower portion of the reactor.

3. Recovering Portion

The recovering portion 3 in accordance with the present invention has, as shown in FIG. 1, a liquid level control portion 30 for keeping a liquid level within the reactor 20 constant and a gas-liquid separating portion 31 for separating the gas-liquid product fed from the control portion 30 into a gas and a liquid.

(1) Liquid Level Control Portion

The liquid level control portion 30 in the present invention communicates respectively with the liquid phase and the gas phase of the reaction product discharged from the reactor 20, thereby keeping the liquid level within the reactor 20 constant.

In the embodiment shown in FIG. 1, a (gas)-liquid feeding tube 32 and a gas introduction tube 33 for communicating the liquid product outlet 24 and the gaseous product outlet 25 provided in the reactor 20, respectively with a liquid product inlet 38 and with a gaseous product inlet 39 provided in the lower portion and in the upper portion.

As a liquid level control tank 34 corresponding to a body portion of the liquid level control portion 30, an overflow type shown in FIG. 1 is convenient and preferable.

By constituting in this manner, even in the case of switching and using only the reacting portion of the catalyst evaluating apparatus already provided, the liquid level can be kept constant without mounting a liquid level sensor or a liquid level control valve.

Incidentally, when a function of controlling the liquid level is given to the gas-liquid separating portion 31 disposed in the later step, which will be mentioned below, and the liquid level control portion can be disposed in a suitable position, that is, the position in which the liquid level of the gas-liquid separating portion 31 is higher than the upper end of the catalyst packing cylinder 57 within the reactor by a degree influenced by the discharge pressure (the fluid head) in the agitator 26, for example, in the case that a set of evaluating apparatus is newly provided, the control tank 34 may not be necessarily provided.

Further, in the case that the liquid product is heavy oil such as atmospheric residual oil and the like, it is preferable to heat the liquid product to a temperature at which it can keep a fluidity in the line.

(2) Gas-liquid separating portion

As the gas-liquid separating portion 31 used in the present invention, as far as the function of separating the reaction product into a gas and a liquid is possessed, there is no special limitation, and in the case that the liquid product is heavy oil such as atmospheric residual oil and the like, it is preferable to heat the liquid product to a temperature at which it can keep a fluidity in the line. In the embodiment shown in FIG. 1, the reaction product discharged from the liquid level control tank 34 is introduced into a gas-liquid separating tank 35 through a gas-liquid feeding tube 36. It is preferable that a liquid level sensor 40 is disposed in the gas-liquid separating tank 35 and a liquid level control valve 58 is disposed the midway of a liquid feeding tube 41. Further, it is preferable that the gas-liquid separating tank 35 separates the reaction product from the gas-liquid feeding tube 36 into a gas and a liquid and a liquid level kept constant by the liquid level control valve 58. Still further, as a position of mounting the gas-liquid separating tank 35, it is suitable as far as the position is lower than a position of the liquid level control tank 34. Furthermore, as mentioned above, without the liquid level control tank 34, the gas-liquid separating tank 35 can be directly connected to the reactor 20. In this case, as an example, it is suitable that the gas introducing tube 33 and the gaseous product outlet line are connected to each other, and the gas-liquid feeding tube 32 and the gas-liquid feeding tube 36 are connected to each other. However, in this time it is necessary to set the position of mounting the gas-liquid separating tank 35 to a position higher than the upper end of the catalyst packing cylinder 57 within the reactor by a degree influenced by the discharging pressure (the fluid head) of the agitator 26.

(3) Evaluating Portion

The reaction product (the gaseous product and the liquid product) separated into a gas and a liquid in the gas-liquid separating tank 35 is introduced into the evaluating portion provided for the purpose of measuring the flow rate, analyzing the composition and so on through a pressure control valve 37 and a cooler (not shown in FIG. 1) respectively disposed in the later step, thereby evaluating the solid catalyst.

Also in this case, in the case that the liquid reacting material is heavy oil such as atmospheric residual oil and the like, it is suitable to heat the line to a temperature capable of keeping the fluidity.

II. Method of Evaluating a Solid Catalyst

A procedure of a method of evaluating a solid catalyst in accordance with an embodiment of the present invention will be described below with reference to FIG. 1. Depending on a purpose of the evaluation, there is no need to necessarily accord with this procedure.

(1) Catalyst Packing

1) The catalyst 23 to be evaluated is packed within the reactor 20.

There is no special limitation on the packing amount of the catalyst and, for example, it can be set to be one particle to several $m^3$. Although it depends on a volume of the reactor, it is preferable to set to a degree of 10 ml to 300 ml. When the packing amount is less than 10 ml, there is a risk that a maldistribution is caused, and when it exceeds 300 ml, there is a risk that the evaluating apparatus exceeds the laboratory scale, so that it becomes expensive.

2) The porous liquid dispersion plate 56 is disposed in the upper portion of the packing cylinder 57 in order to prevent the maldistribution.

3) The cover 55 of the reactor is closed.

(2) Leak Test

1) The pressure in the reactor 20 is increased to a level equal to or higher than a reaction pressure by using a suitable gas, thereby confirming that there is no leakage and no pressure reduction.

(3) Wetting

1) A predetermined amount of gaseous raw material is fed from the raw material feeding portion 1 in accordance with a desired evaluation condition.

2) The reaction temperature is increased in accordance with the desired evaluation condition.

3) A predetermined amount of liquid raw material is fed from the raw material feeding portion 1 in accordance with the desired evaluation condition.

4) It is recognized that the reactor 20 is filled with the liquid raw material, the catalyst is wetted, the liquid level control tank 34 becomes a predetermined liquid level and the gas-liquid separating tank 35 reaches a predetermined liquid level.

As a temperature at this time, it is preferable that it is a temperature equal to or higher than a temperature at which the liquid raw material flows and a temperature equal to or lower than a temperature at which the catalyst 23 does not react with the liquid raw material.

At a temperature lower than a flowing point there is a risk that the agitator 26 is broken, and at a temperature at which the reaction occurs, there is a risk that the reaction is excessively proceeded on the catalyst surface and thus the catalyst is deteriorated because the flowing has not started yet.

5) It is necessary to make the liquid level of the liquid level control tank 34 higher than the upper end of the catalyst packing cylinder 57 within the reactor by a degree influenced by the discharge pressure (the fluid head) in the agitator 26.

When the liquid level is low, the liquid raw material is not circulated or even when it is circulated, it is intermittently fed to the catalyst. Further, when the liquid level is high, the gas is not stored in the upper portion of the reactor, so that a gas-liquid interface area is largely reduced.

6) After confirming the above item 4), the agitator 26 is rotated in accordance with the desired evaluating condition and the liquid raw material is brought into contact with the solid catalyst under a state of a liquid phase flow or a gas-liquid two phase flow.

(4) Pre-Treatment of the Catalyst

1) In accordance with the desired evaluating condition, a pre-treatment of the catalyst is performed. As the pre-treatment, there are, for example, a catalytic reduction, a catalytic pre-sulfurization and the like. On the basis of the characteristic of the tank reactor, considering the fact that the reaction efficiency thereof is lower than that of the tubular type, it is preferable to select a condition which is somewhat more excessive than the tubular reactor.

For example, there are exemplified that a temperature for the pre-treatment temperature is made high, a time for the pre-treatment is made long, a raw material for the pre-treatment is fed somewhat in a large amount, and so forth.

(5) Evaluation of Reaction

1) The reaction product is continuously discharged from the recovering portion 3 and an evaluation of the catalyst is performed in accordance with the desired evaluating condition.

(6) Shut Down of the Apparatus

1) When the evaluation of reaction is completed, the reaction temperature is decreased.

2) If necessary, the liquid raw material is replaced by a detergent.

3) When the temperature is decreased to a safety temperature, the feed of the liquid raw material is stopped.

4) The gaseous raw material is replaced by an inert gas, etc. and the inner portion of the reacting apparatus is substituted.

5) The rotation is stopped and the pressure is extracted.

Incidentally, since inmost of the internal recycle reactors, the gas is not circulated under a atmospheric pressure (when the specific gravity of the gas is low, the agitating effect becomes low and so the internal circulation does not occur), it is preferable to perform the pressure extraction at the last time.

(7) Analysis of the Reaction Results

1) The results of evaluating the catalyst in the internal recycle reactor are analyzed as the tank type (a continuous stirred tank reactor).

2) A reaction rate constant is obtained by a suitable order of reaction and its conversion to the tubular type is performed.

The present invention will be further concretely described below with reference to Examples.

EXAMPLE 1

(Evaluating Apparatus)

The catalyst is evaluated on the basis of the evaluating apparatus having a constitution shown in FIG. 1. The main constitutional elements used are as follows.

Internal recycle reactor: The one in which a modification is added to 3 inches Berty reactor manufactured by AUTOCLAVE ENGINEER COMPANY in such a manner as shown in FIG. 2.

Catalyst to be evaluated: Heavy oil hydrocracking catalyst A (Co—Mo system/Alumina+USY, 1/16 inches trilobed type) 15, 50 ml packing Raw material oil: Dibenzothiophene+n-tridecane (both are special grade test reagents) is prepared to have a sulfur concentration of 0.3 weight percents.

(Pre-Treatment of the Catalyst)

In the pre-treatment of the catalyst, a pre-sulfurization is performed under the following conditions.

Sulfurization agent: non-desulfurized light gas oil having a sulfur concentration of 1.16weight percents and the specific gravity of 0.8430

Pressure: 115 kg/cm$^2$G

Sulfurization temperature: 260 ° C.

LHSV: 1.0 1/h

Sulfurization time: 24 hours

Hydrogen/oil ratio: 1000 Nm$^3$/kl (Reaction Condition)

The reaction in the reactor is performed under the following conditions.

Pressure: 100 kg/cm$^2$G

Reaction temperature: 200 to 300° C.

LHSV: 1 to 10 1/h

Hydrogen/oil ratio: 2000 Nm$^3$/kl

Rotating speed of agitator: 1000 rpm

Estimating value of superficial liquid linear speed: 6 cm/s (when a packing amount of the catalyst is 50 ml) and 11 cm/s (when a packing amount of the catalyst is 15 ml)

(Evaluation Results)

The conversion of desulfuration is obtained from a sulfur concentration at the inlet and the outlet of the reactor.

Figure 3:
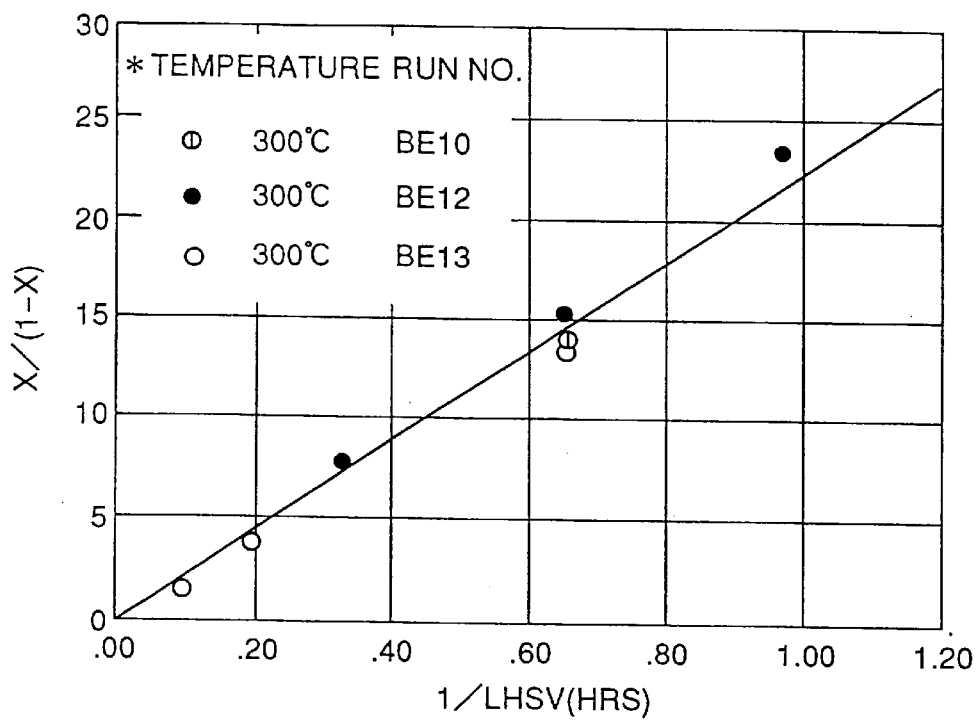
FIG. 3 is an explanatory view which shows a relation between 1/LHSV, that is, a residence time and a conversion of desulfurization (X) in the evaluation of the catalyst in the present invention.

FIG. 3 shows a relation between 1/LHSV (that is, a residence time) and the conversion of desulfuration (X).

As shown in FIG. 3, it is understood that the conversion of desulfuration (X) is dependent on a first order reaction rate of the tank reactor over a wide range of the LHSV.

First order reaction rate equation of the tank reactor:

$$k = \text{LHSV} \times X/(1-X) \tag{1}$$

First order reaction equation of the tubular reactor:

$$k = \text{LHSV} \times \{-\ln(1-X)\} \tag{2}$$

The reaction rate constant k is obtained by the above equation (1).

Figure 4:
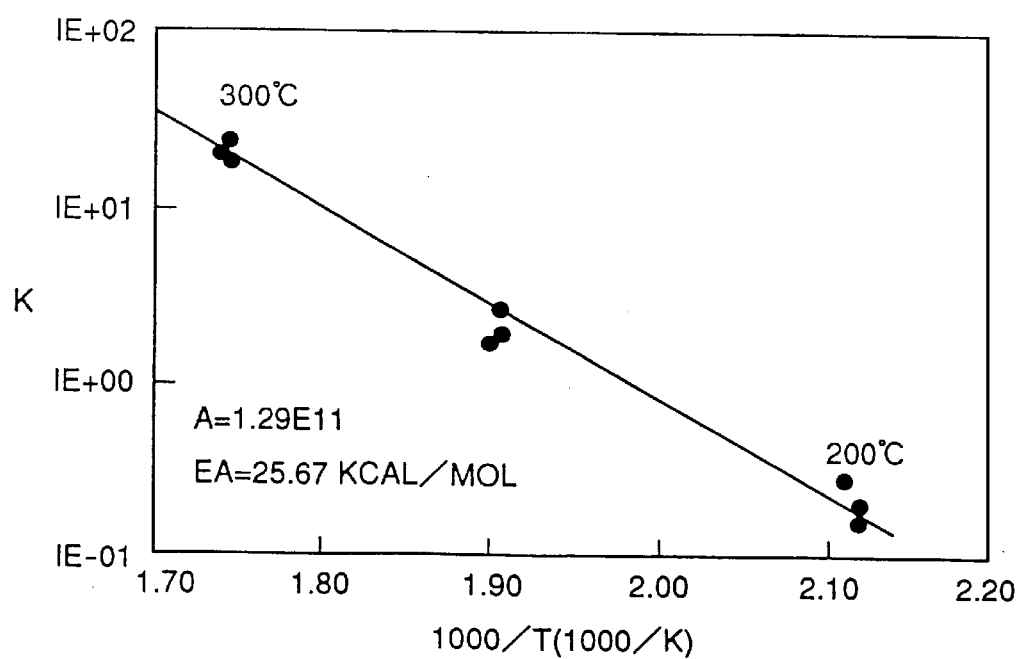
FIG. 4 is an explanatory view which shows Arrhenius plots of a first order reaction rate constant obtained in the evaluation of the catalyst in the present invention.

FIG. 4 shows Arrhenius plots of the obtained first order reaction rate constants.

The drawing shows a linear relation and Ea=25.7 kcal/mol is obtained as an activation energy.

As mentioned above, from the fact that the conversion of desulfuration is dependent on the first order reaction rate equation, that the Arrhenius plots become linear and that the activation energy becomes a value showing a reaction rate-determining, it is understood that this evaluating method gives appropriate results.

Comparison Example 1
(Evaluating Apparatus)

Under a state that in the reactor of Example 1, the internal recycle reactor is replaced by an isothermal tubular reactor, the evaluation is performed by the following structure.

Isothermal tubular reactor: A tube type having a thermowell of an outer diameter of 6.35 mm in the center portion and having an inner diameter of 19 mm and a length of 1.2 m Catalyst to be evaluated: The same catalyst A as Example 1 is packed in an amount of 50 ml.

Raw material oil: The same as Example 1
(Pre-Treatment of the Catalyst)

In the pre-treatment of the catalyst, a pre-sulfurization is performed under the following conditions.

Pressure: 135 kg/cm$^2$G

The other conditions are the same as Example 1.
(Reaction Condition)

The reaction in the reactor is performed under the following conditions.

Reaction temperature: 275 ° C.

LHSV: 1 to 3 1/h

Superficial liquid linear velocity: 2E-3 cm/s (when the LHSV =1) and 6E-3 cm/s (when the LHSV =3)

Pressure and hydrogen/oil ratios are the same as Example 1.
(Evaluation Results)

Table 2 shows a comparison between Example 1 and Comparison example 1 in terms of the evaluation results (X=a conversion of desulfuration [%] of dibenzothiophene in n-tridecane). The evaluation results of Example 1 in Table 2 is the one converted into the conversion of desulfuration in the tubular type by the first order reaction rate equation (2) of the tubular type from the obtained speed constant.

In Comparison example 1, since in the tubular reactor the superficial liquid linear speed is lower than one thousandth in comparison with Example 1, it is understood that a correct reaction result can not be obtained due to the influence of the material movement.

Comparison Example 2

Except the fact that, in Comparison Example 1, as a catalyst to be evaluated in the isothermal tubular reactor the one mentioned below is used and the flow is improved by packing a catalyst diluted with fine particles, the evaluation is performed in the same manner as Comparison Example 1.

Catalyst to be evaluated: The same catalyst A as Example 1 in an amount of 50 ml and 32–64 mesh silicon carbide in an amount of 50 ml are alternately packed little by little.
(Evaluation Results)

Table 2 shows comparison & between Example 1, Comparison example 1 and the Comparison example 2.

In the Comparison example 2, although it is recognized that the conversion of desulfuration is slightly improved in Comparison with the comparison example 1 due to the effect that the catalyst is diluted with the fine particles (this effect mainly suppresses an influence of an back mixing), the desulfuration rate is significantly lower in comparison with Example 1, so that it is understood that there is a limitation in the tubular reactor in comparison with the internal recycle type.

TABLE 2

| LHSV (1/h) | Example 1 | Comparison Example 1 | Comparison Example 2 |
| --- | --- | --- | --- |
| 1.0 | 99.9 | 90.9 | 96.8 |
| 1.5 | 99.3 | 83.3 | 90.8 |
| 2.0 | 97.6 | 80.3 | 84.8 |
| 3.0 | 91.8 | 70.0 | 73.0 |

Note: Example 1 shows results obtained by of estimating into a conversion of desulfuration in the tubular type from a reaction rate constant of the tank type.

EXAMPLE 2
(Evaluating Apparatus)

Except that heavy oil mentioned below is used instead of the raw material in Example 1, the same apparatus as Example 1 is used. However, the catalyst to be evaluated is packed in an amount of 50 ml.

Raw material oil: Atmospheric residual oil of Arabian heavy crude oil (the characteristic thereof is shown in Table 3)
(Pre-Treatment of the Catalyst)

In the pre-treatment of the catalyst, a pre-sulfurization is performed under the following conditions.

Sulfurization agent: non-desulfurized light gas oil having a sulfur concentration of 1.16 weight percents and the specific gravity of 0.8430

Pressure: 130 kg/cm$^2$G

Sulfurization temperature: 250 ° C.

LHSV: 1.0 1/h

Sulfurization time: 24 hours

Hydrogen/oil ratio: 1000 Nm$^3$/kl
(Reaction Condition)

The reaction in the reactor is performed under the following conditions.

Pressure: 130 kg/cm$^2$G

Reaction temperature: 380 -C

LHSV: 0.3 to 1.0 1/h

Hydrogen/oil ratio: 700 Nm$^3$/kl

Rotating speed of agitator: 1000 rpm

Estimating value of superficial liquid linear velocity: 4 cm/s
(Evaluation Results)

The conversion of desulfuration and the conversion of hydrocracking are obtained from the sulfur concentration at the outlet and the inlet of the reactor and from the weight content of fraction having a temperature equal to or higher than 343° C. and measured by a distillation gas chromatography.

Figure 5:
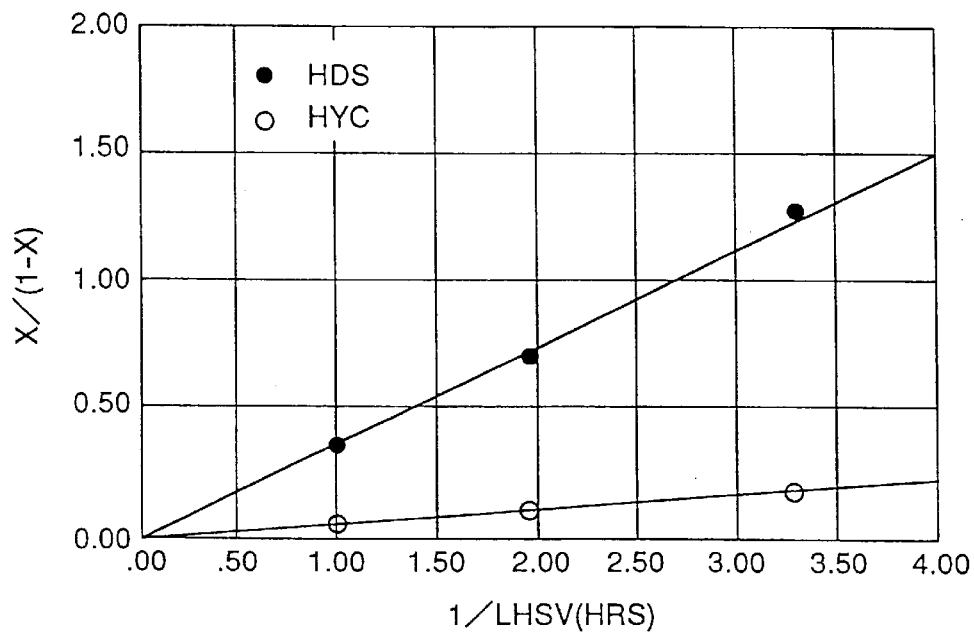
FIG. 5 is an explanatory view which shows relations between 1/LHSV, that is, a residence time, a conversion of desulfurization (HDS) and a conversion of hydrocracking (HYC) in the evaluation of the catalyst in the present invention.

FIG. 5 shows relations between 1/LHSV (that is, a residence time), the conversion of desulfuration (HDS) and the conversion of hydrocracking (HYC). According to FIG. 5, it is understood that the HDS and the HYC are dependent on the first order reaction rate equation of the tank reactor over a wide range of the LHSV, and so it is understood that this evaluating method can give appropriate results also in the reaction of the heavy oil.

TABLE 3

| | |
| --- | --- |
| Specific gravity (–) | 0.9798 |
| Kinematic viscosity @ 50° C. (cSt) | 1098 |
| Sulfur content (wt. %) | 4.13 |
| Nitrogen content (ppm) | 2500 |

TABLE 3-continued

| | |
|---|---|
| V content (ppm) | 85 |
| Ni content (ppm) | 26 |
| Micro residual carbon content (wt. %) | 14.7 |
| n-Heptane insoluble content (wt. %) | 7.67 |

Comparison Example 3
(Evaluating Apparatus)

Except that the reactor used in Example 2 is replaced by an isothermal tubular reactor mentioned below is used, the same apparatus as Example 2 is used.

Isothermal tubular reactor: A tube type having a thermowell of an outer diameter of 7.94 mm in the center portion and having an inner diameter of 25 mm and a length of 3.5 m Catalyst to be evaluated: The same catalyst A as Example 1 is filled in an amount of 700 ml.

Raw material oil: The same as Example 2
(Pre-Treatment of the Catalyst)

In the pre-treatment of the catalyst, a pre-sulfurization is performed under the following conditions.

LHSV: 0.8 l/h

The other conditions are the same as those of Example 2.
(Reaction Condition)

The reaction in the reactor is performed under the following conditions.

Reaction temperature: 380 ° C.

LHSV: 0.3 1/h

Superficial liquid linear velocity: 0.02 cm/s

Pressure and hydrogen/oil ratios are the same as Example 1.
(Evaluation Results)

Figure 6:
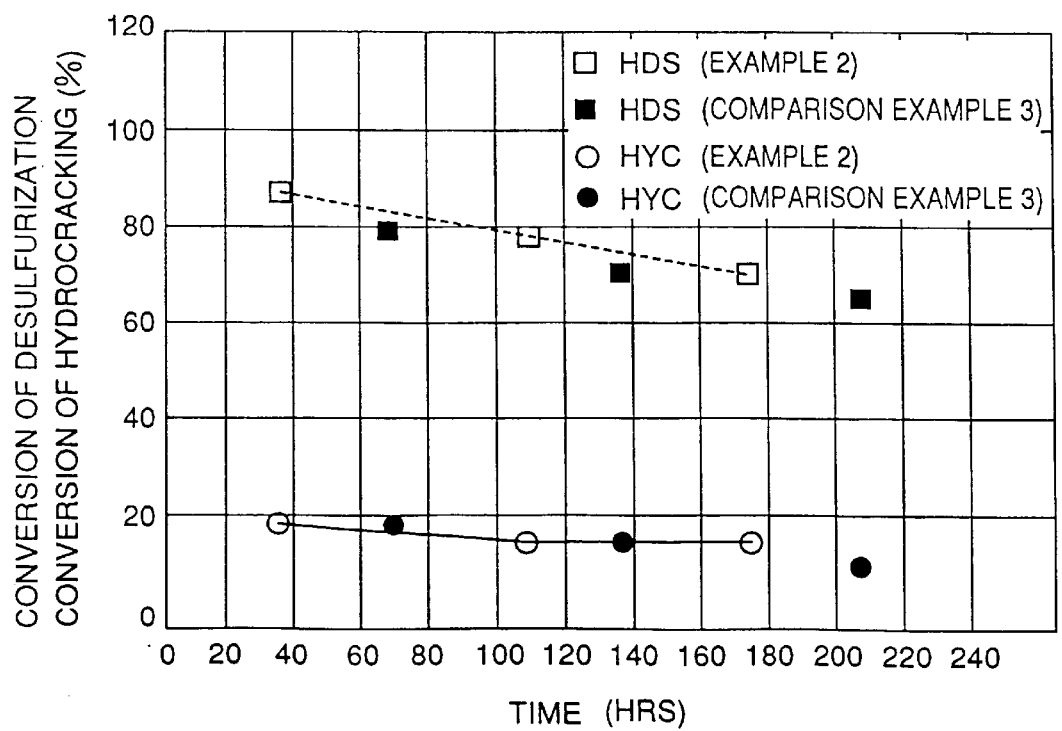
FIG. 6 is an explanatory view which shows a comparison of evaluated results of the conversion of desulfurization (HDS) and the conversion of hydrocracking (HYC) in Example 2 and Comparison Example 3.

FIG. 6 shows a comparison in terms of results of evaluating the HDS and the HYC with Example 2. The evaluation result of Example 2 in FIG. 6 is the one estimated the HDS and the HYC in the tubular type by the first order reaction rate equation (2) of the tubular type from the rate constant obtained by the tank type.

The results of evaluating the HDS and the HYC in Example 2 and Comparison Example 3 substantially agree with each other, and it is considered that both become in the same result because in the tubular reactor the superficial liquid linear velocity in the tubular reactor is equal to or less than one two hundreds and fiftieth in comparison with Example 2 but the reaction rate is lower in comparison with Example 1 and the like.

As mentioned above, in the desulfuration reaction and the hydrocracking reaction of the atmospheric residual oil, it is understood that the evaluating method in accordance with the present invention and the isothermal tubular reactor of the relatively large size both give an appropriate result, so that it is shown that the evaluating method in accordance with the present invention not only gives an appropriate result but also is useful for scale-up of a plant.

As described above, according to the present invention, there are provided an apparatus of evaluating the solid catalyst and a method for evaluating the solid catalyst, in which the range of the applied fluid used for evaluating the performance of the solid catalyst is enlarged from the gas phase to the liquid phase or the gas-liquid phase and the performance of the solid catalyst can be accurately evaluated by a small scale laboratory apparatus.

Further, according to the present invention, in developing a new plant, a step of a large size experimental apparatus (a demo plant, a pilot plant or the like) can be omitted.

While the invention has been described in detail and with reference to specific embodiments thereof, it will be apparent to one skilled in the art that various changes and modifications can be made therein without departing from spirit and scope thereof.

What is claimed is:

1. An apparatus comprising a raw material feeding portion for feeding a fluid raw material;

a reacting portion having a reactor for catalytically converting the fluid raw material into a reaction product, the reactor including a means disposed within the reactor for circulating the fluid raw material and a portion of the reaction product inside the reactor into contact with a fixed catalyst disposed within the reactor; and a recovering portion for recovering a portion of the reaction product fed from the reacting portion, wherein the raw material feeding portion has a function capable of continuously feeding a liquid raw material or a mixed raw material consisting of a gas and a liquid, the reactor in the reacting portion has an inlet for the fluid raw material and reaction product outlets for discharging the reaction product while separating it respectively into a liquid product and a gaseous product, the recovering portion has reaction product inlets connected to each of the reaction product outlets of the reactor and has a liquid level control portion for keeping a liquid level within the reactor constant.

2. The apparatus according to claim 1, wherein the recovering portion further comprises a gas-liquid separating portion for separating a reaction product fed out from the liquid level control portion into a gas and a liquid.

3. The apparatus according to claims 1 or 2, wherein the reactor in the reacting portion is a fixed catalyst internal recycle reactor.

4. The apparatus according to claims 1 or 2, wherein the liquid level control portion is an overflow control tank.

5. The apparatus according to claim 1, wherein the means for circulating is a fluid impeller.

6. The apparatus according to claim 1, wherein the fixed catalyst is disposed in a single catalyst bed within the reactor.

7. The apparatus of claim 6, wherein the reactor is a fixed catalyst internal recycle reactor.

8. The apparatus of claim 6, wherein the fixed catalyst is disposed in a single catalyst bed within the reactor.

9. A method of evaluating a solid catalyst, the method comprising providing the apparatus of claims 1 or 2, bringing a fluid raw material into the reacting portion of the apparatus and into contact with a fixed catalyst, and continuously discharging a reaction product.

10. The method according to claim 5, wherein the fluid raw material comprises at least one of the group consisting of oils and hydrogen.

11. An apparatus comprising a raw material feeding portion;

a reacting portion connected to the raw material feeding portion; and a recovering portion connected to the reacting portion, wherein the reacting portion comprises a reactor including a fluid impeller disposed within the reactor and a fixed catalyst disposed within the reactor;

the reactor comprises a liquid product outlet and a gaseous product outlet; and the recovering portion comprises a liquid product inlet connected to the liquid product outlet of the reactor, a gaseous product inlet connected to the gaseous product outlet of the reactor, and a liquid level control portion for keeping a liquid level within the reactor constant.

\* \* \* \* \*